(12) United States Patent
Denley

(10) Patent No.: US 7,585,109 B2
(45) Date of Patent: Sep. 8, 2009

(54) ARM LINKAGE SYSTEM FOR A RADIOGRAPHIC DEVICE

(75) Inventor: Ronald S. Denley, Woodstock, IL (US)

(73) Assignee: X-Cel X-Ray, Crystal Lakes, IL (US)

( * ) Notice: Subject to any disclaimer, the term of this patent is extended or adjusted under 35 U.S.C. 154(b) by 0 days.

(21) Appl. No.: 11/943,870

(22) Filed: Nov. 21, 2007

(65) Prior Publication Data

US 2009/0129554 A1 May 21, 2009

(51) Int. Cl.
*H05G 1/02* (2006.01)
(52) U.S. Cl. .......................... 378/197; 378/193
(58) Field of Classification Search .......... 378/192, 378/193, 195–198, 205; 248/324, 325
See application file for complete search history.

(56) References Cited

U.S. PATENT DOCUMENTS

| | | |
|---|---|---|
| 1,184,503 A | 5/1916 | Alden |
| 1,239,145 A | 9/1917 | Wantz |
| 1,913,695 A | 6/1933 | Werner |
| 2,307,612 A | 1/1943 | Westendorp |
| 3,801,790 A | 4/1974 | Götzl et al. |
| 4,166,602 A | 9/1979 | Nilsen et al. |
| 4,223,230 A | 9/1980 | Waerve et al. |
| 4,250,388 A | 2/1981 | Janu |
| 4,302,675 A | 11/1981 | Wake et al. |
| 4,326,131 A | 4/1982 | Waerve |
| 4,335,315 A | 6/1982 | Waerve et al. |
| D273,892 S | 5/1984 | Fenne et al. |
| 4,532,645 A | 7/1985 | Morris |
| 4,577,340 A | 3/1986 | Carlson et al. |
| 4,587,668 A | 5/1986 | Morris |
| 4,590,378 A | 5/1986 | Platz |
| 4,694,151 A | 9/1987 | Yoshimura |
| 4,694,480 A | 9/1987 | Skillicorn |
| D294,915 S | 3/1988 | Alonso |
| 4,752,948 A | 6/1988 | MacMahon |
| 4,775,994 A | 10/1988 | Kranvogel |
| 4,887,287 A | 12/1989 | Cobben |
| 4,989,229 A | 1/1991 | Negrelli et al. |
| 5,081,662 A | 1/1992 | Warden et al. |
| 5,283,823 A | 2/1994 | Morris |
| 5,388,142 A | 2/1995 | Morris |
| 6,683,439 B2 | 1/2004 | Takano et al. |

*Primary Examiner*—Jurie Yun
(74) *Attorney, Agent, or Firm*—Miller, Matthias & Hull

(57) ABSTRACT

A radiographic device may include a base, a support arm pivotably coupled to the base and defining a support axis, the support arm being movable between a normal position and two diametrically opposed, laterally rotated positions, and a radiographic head coupled to the support arm. A tension assembly may be coupled to the base and a linkage system may extend between the tension assembly and the support arm. The linkage system may include a hub and linkage may be partially entrained with the hub. The linkage may include a pivot point joining the linkage proximal end and the linkage distal end. When the support arm is in the normal position, the linkage may be positioned with respect to the hub so that the lateral reference line also intersects the linkage pivot point.

18 Claims, 7 Drawing Sheets

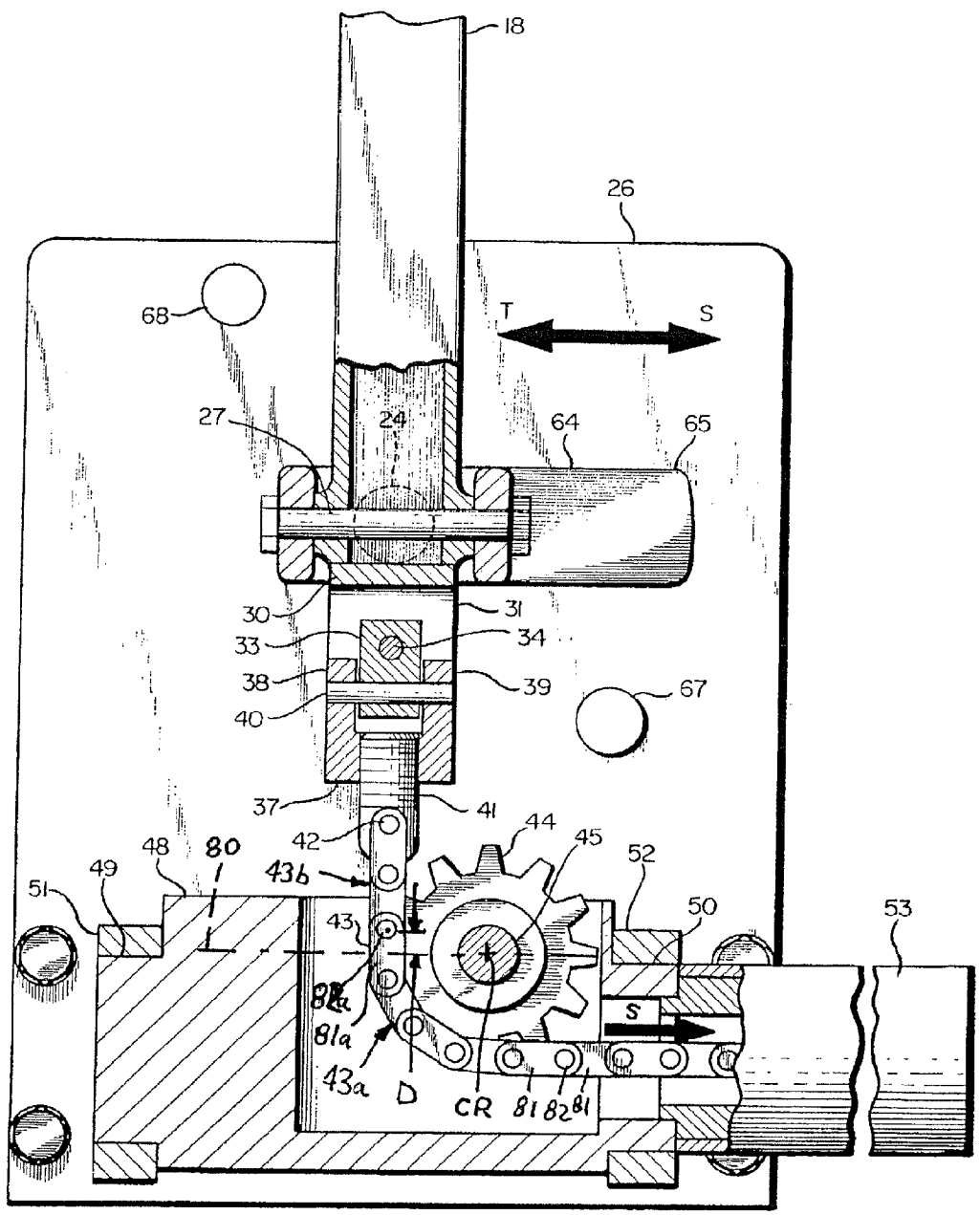

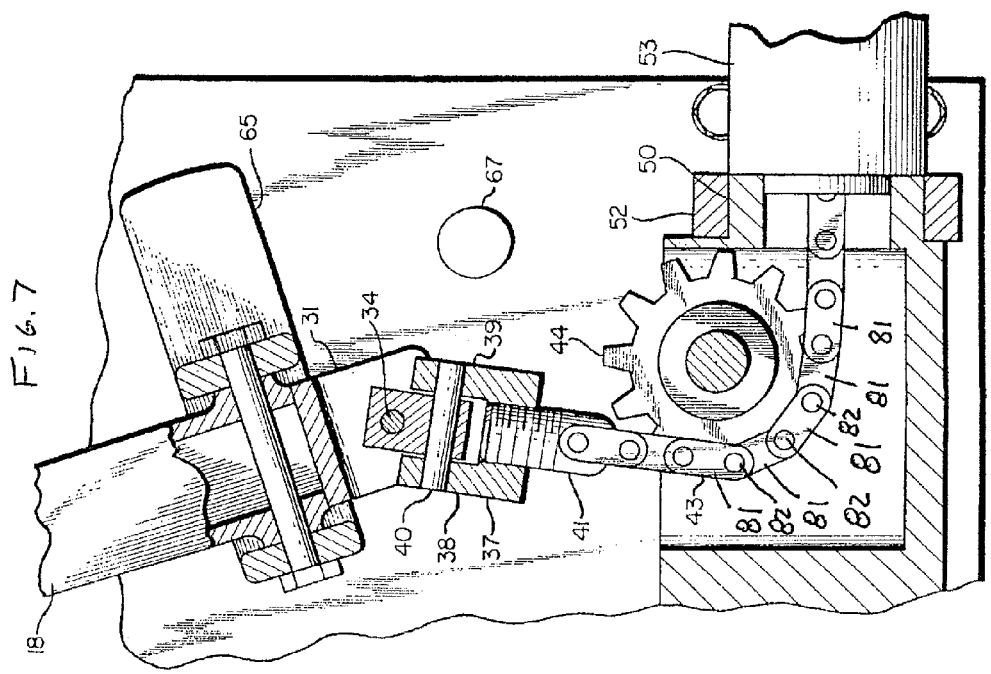
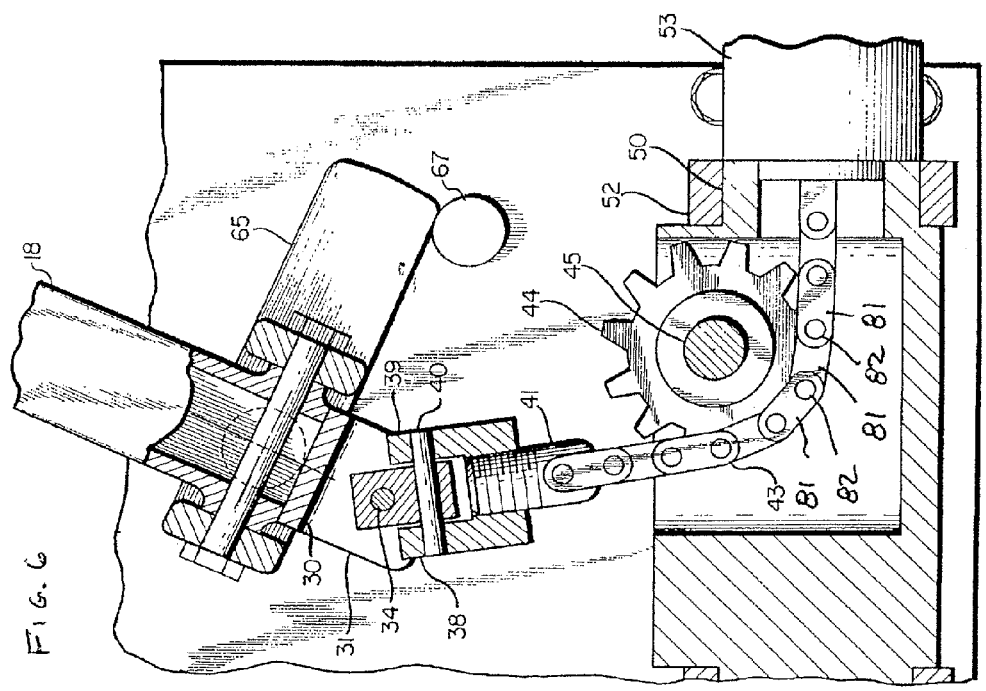

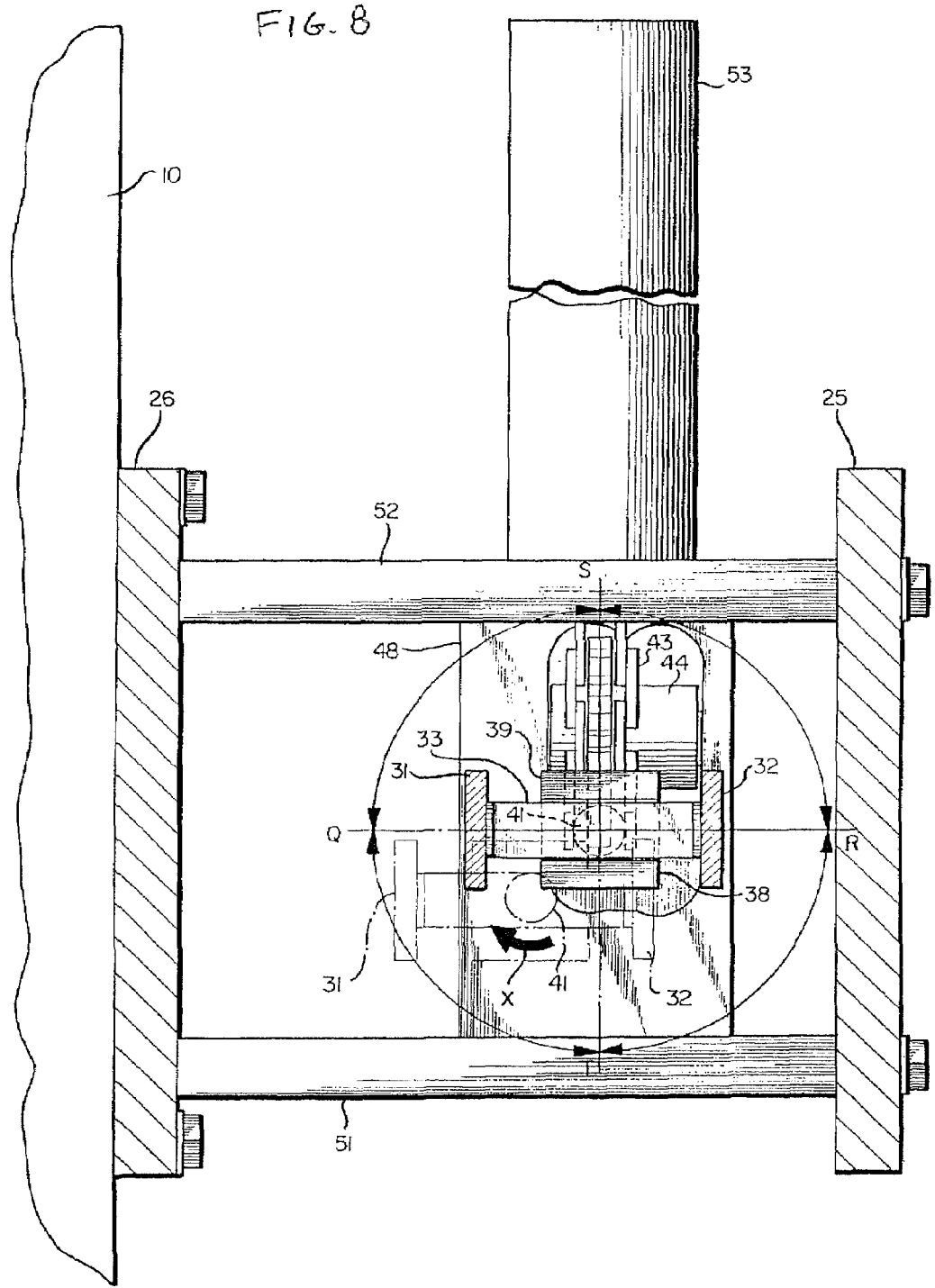

ARM LINKAGE SYSTEM FOR A RADIOGRAPHIC DEVICE

BACKGROUND

1. Technical Field

This disclosure generally relates to radiographic imaging systems and methods, and more particularly to linkages used in such devices for holding support arms in desired positions.

2. Description of the Related Art

Various types of radiographic devices are generally known in the art. A known x-ray unit for podiatry is disclosed in U.S. Pat. No. 4,587,668, which is assigned to the same assignee as the present disclosure. Generally, such x-ray units include a platform upon which a patient places his or her feet to be x-rayed. The platform is raised above floor level to allow film cassettes to be positioned in a film well located below the platform. The platform may further include a slot for receiving a vertically oriented film cassette. A radiographic head is mounted on vertical mounting members, which serve to space the radiographic head a desired distance above the foot platform. The vertical mounting members are moveable in both the lateral and longitudinal directions so that x-rays of a patient's feet can be taken from many angles while easily maintaining the same source to image distance (SID).

Known radiographic devices typically use means, such as a spring assembly, to hold the mounting members and radiographic head in the desired position. The spring assembly is coupled to the mounting members by a linkage system. The '668 patent discloses a linkage system comprising a chain partially entrained about a rotatable hub. With the mounting members in a normal position, in which they are substantially vertically aligned, the spring system assumes a first or contracted position. When the mounting members are moved laterally, however, the spring assumes a compressed position to counteract the bending moment created by the weight of the radiographic head.

The aforementioned spring assembly and linkage adequately supported mounting members used in previously known radiographic devices, such as the device disclosed in the '668 patent. More recently, however, it has been proposed to lengthen the mounting members so that the radiographic devices can take a wider variety of images at a longer SID. More specifically, devices with shorter mounting members, such as approximately 28 inches or less, are typically useful for taking either foot or arm images, but not both. When the mounting members are lengthened to approximately 40 inches, however, the radiographic device may be easily adjusted to take images of both the foot and arm extremities. The increased length, however, creates a larger moment arm on which the weight of the radiographic head acts, thereby increasing the magnitude of the force that the spring assembly must counter to hold the mounting members in place. The previously known linkage assemblies do not adequately compensate for this increased force, and instead have demonstrated a tendency to at least partially return the mounting arms to the normal position when they are initially placed in the extreme lateral positions. Such "snap back" causes inaccuracies in the angle at which the radiographic head is placed and can require additional time for the radiograph technician to properly place the head.

SUMMARY OF THE DISCLOSURE

A radiographic device may include a base, a support arm pivotably coupled to the base and defining a support axis, the support arm being movable between a normal position and two diametrically opposed, laterally rotated positions, and a radiographic head coupled to the support arm. A tension assembly may be coupled to the base and a linkage system may extend between the tension assembly and the support arm. The linkage system may include a hub rotatably coupled to the base and defining a center of rotation with which a lateral reference line intersects. A linkage may be partially entrained with the hub and may have a proximal end adapted for coupling to the support arm and a distal end adapted for coupling to the tension assembly. The linkage may include a pivot point joining the linkage proximal end and the linkage distal end. When the support arm is in the normal position, the linkage may be positioned with respect to the hub so that the lateral reference line also intersects the linkage pivot point.

According to additional aspects, a linkage system for a radiographic device may be provided. The radiographic device may include a base, a support arm pivotably coupled to the base and defining a support axis, wherein the support arm being movable between a normal position and two diametrically opposed, laterally rotated positions, a radiographic head coupled to the support arm, and a tension assembly coupled to the base. The linkage system extends between the tension assembly and the support arm and may include a hub rotatably coupled to the base and defining a center of rotation with which a lateral reference line intersects. A linkage is partially entrained with the hub and has a proximal end adapted for coupling to the support arm and a distal end adapted for coupling to the tension assembly, wherein the linkage includes a pivot point joining the linkage proximal end and the linkage distal end. When the support arm is in the normal position, the linkage is positioned with respect to the hub so that the lateral reference line also intersects the linkage pivot point.

BRIEF DESCRIPTION OF THE DRAWINGS

For a more complete understanding of the disclosed methods and apparatuses, reference should be made to the embodiment illustrated in greater detail on the accompanying drawings, wherein:

FIG. 5 is a fragmentary section view of a mounting assembly with the linkage oriented in a manner shown in the prior art;

FIG. 6 is a fragmentary section view of the mounting assembly of FIG. 5 but with the vertical mounting members pivoted at an acute angle from the vertical axis whereby the radiographic head is disposed closer to the spring assembly than the normal position of FIG. 5;

FIG. 7 is a fragmentary section view of the mounting assembly of FIG. 6 except that the mounting members are disposed at an acute angle opposite that shown in FIG. 6;

FIG. 8 is a fragmentary, plan section view of the mounting assembly of the present invention taken along lines 8-8 of FIG. 2.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION

This disclosure relates to linkages used in radiographic devices to hold Support arms in desired positions. Radiographic devices may include a platform upon which the desired target area of a patient is placed. Mounting members are pivotably coupled to the base and carry a radiographic head. The mounting members permit the radiographic head to be placed at various orientations with respect to the platform, thereby to obtain radiographic images from various angles. It is common for such devices to allow the mounting members to rotate from an upright, normal position, to two diametrically opposed, lateral positions. A spring assembly is coupled to the mounting members to hold them in the desired position. A flexible linkage is entrained in a rotatable hub and couples the spring assembly to the mounting members. The flexible linkage includes a pivot point about which the flexible linkage may bend. When the mounting members are in the normal positions, the pivot point of the flexible linkage is aligned with a lateral reference line extending through a center point of the hub, thereby to optimize the range of moment arm forces that are generated as the mounting members traverse their entire range of motion. As a result, the spring assembly more reliably holds the support arm in both diametrically opposed positions.

The radiographic device of the present disclosure is similar to that disclosed in U.S. Pat. No. 4,587,668, which has the same assignee as the present disclosure and is incorporated herein by reference. The primary difference between the present device and that of the '668 patent lies in the linkage assembly and orientation, described in greater detail below with reference to FIG. 9. Prior to that description, however, we will describe an exemplary radiographic device in which such a linkage assembly may be used.

Figure 1:
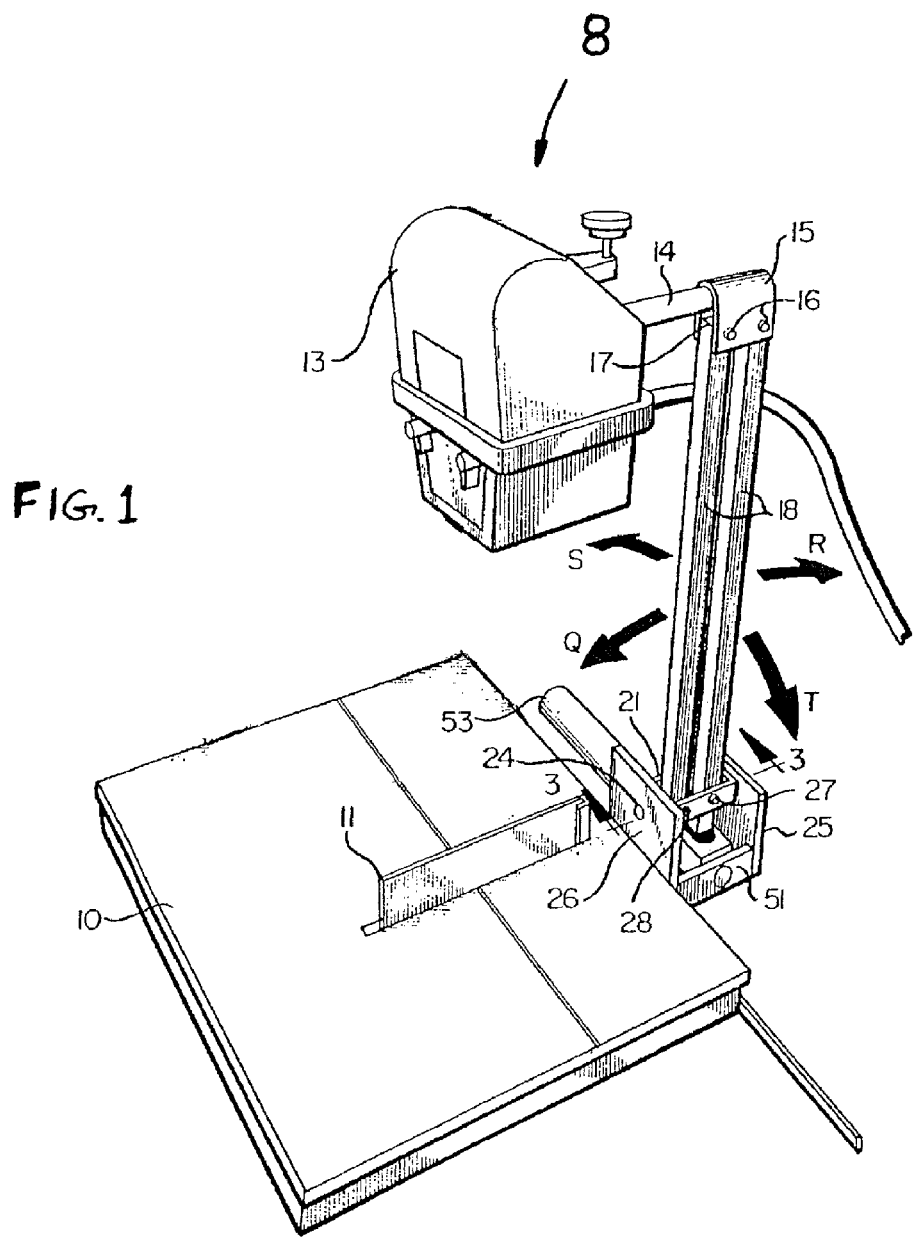
FIG. 1 is a perspective view of a radiographic device constructed in accordance with the teachings of the disclosure.

Referring now to the drawings, and with specific reference to FIG. 1, a radiographic device is generally referred to by reference numeral 8. The radiographic device 8 is described and illustrated herein for use in podiatry treatment, but the teachings provided herein may be applied to radiographic devices used in other fields.

The radiographic device 8 includes a patient platform 10 and a removable foot separation plate 11 extending perpendicular to the platform 10. A film cartridge may be inserted either in the foot separation plate 11 or a tray positioned below the platform 10, depending upon the desired x-ray view. While not shown, hand rail legs may be mounted to the platform 10 to provide a patient support hand rail.

A radiographic head 13 is mounted, as shown in FIG. 1, on one end of an arm 14 while the remaining end of arm 14 is joined to a U-shaped mounting plate 15 which is bolted at 16 to the upper ends 17 of a pair of vertical mounting members 18.

Figure 2:
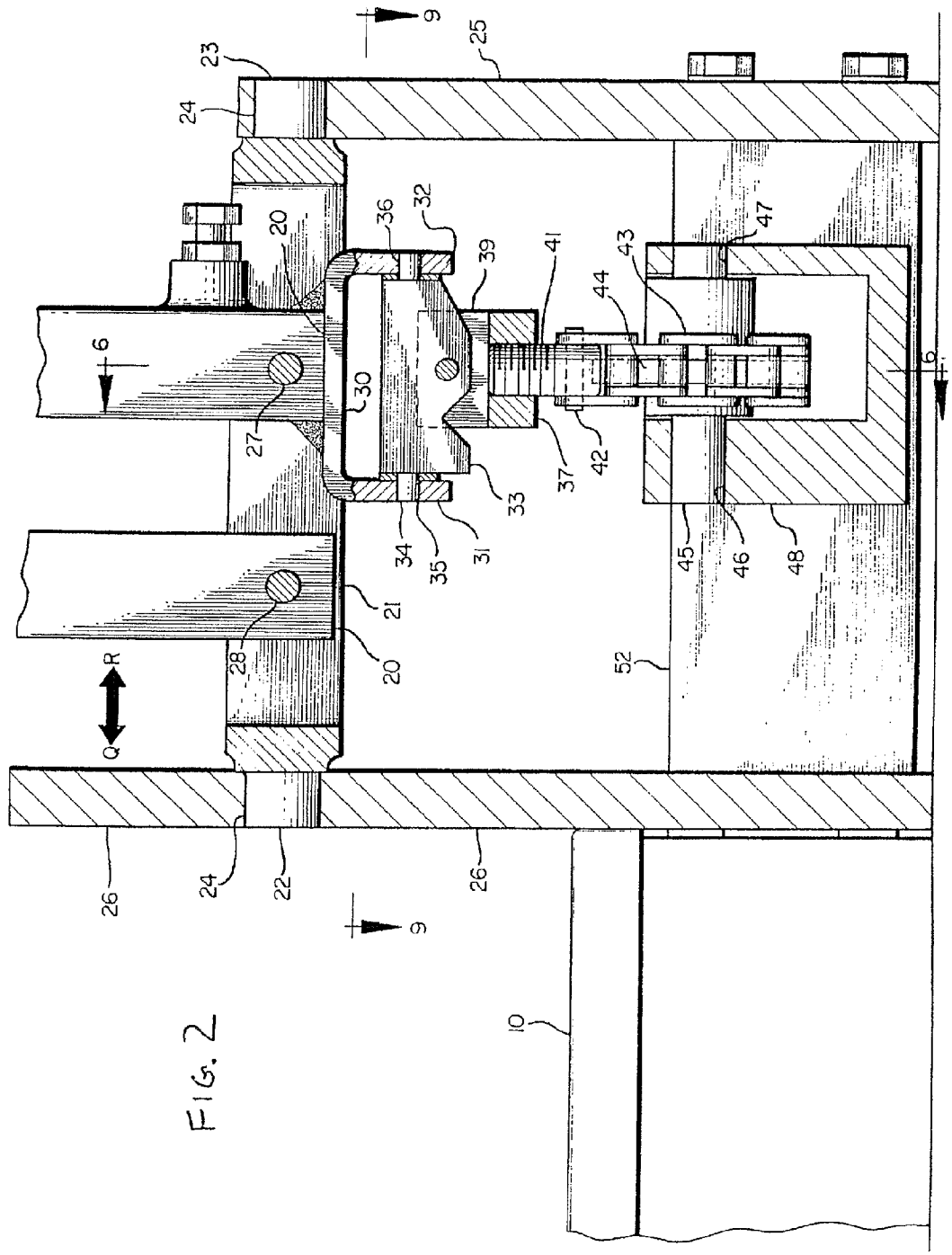
FIG. 2 is a fragmentary section view of a mounting assembly used to mount the radiographic device along line 2-2 of FIG. 1.

As shown in FIGS. 1 and 2, the lower ends of the vertical mounting members 18 are disposed in a rectangular shaped trunnion or frame 21. The trunnion 21 includes hubs 22, 23 which are pivotally connected at 24 to frame mounting plates 25, 26. Mounting members 18 are pivotally connected by any suitable pivot means such as bolt and nut assemblies 27, 28 to trunnion 21 whereby members 18 pivot about pins 27, 28 in the direction of the arrows "Q" and "R", shown in FIGS. 1 and 2, and trunnion 21 also is adapted to pivot about hubs 22, 23 in the direction of arrows "S" and "T", shown in FIGS. 1 and 5.

Referring to FIGS. 2 and 5, a first yoke 30 having yoke arms 31, 32 is attached to an end 20 of one of the vertical mounting members 18. A block 33 having a pin 34 disposed therethrough is pivotally mounted at 35, 36 to the yoke arms 31, 32. A second yoke 37 having yoke arms 38, 39 is pivotally connected to block 33 by means of a pivot pin 40 which extends through block 33 and yoke arms 38, 39.

A fastener 41 is threaded into second yoke 37 as shown, for example, in FIGS. 2 and 5. The fastener 41 is connected by means of a pin 42 to one end of a chain 43 which is adapted to move on a rotatable hub, such as a chain sprocket member 44.

A sprocket shaft 45 passes through the sprocket member 44 and is pinned to a sprocket block 48 at 46, 47. As shown in FIGS. 2-5, the sprocket block 48 includes hubs 49, 50 which are seated for rotation in lower mounting frame members 51, 52 which are joined to frame plates 25, 26.

The remaining end of the chain 43 is fastened to one end of a compression spring, which is disposed in a conventional spring assembly 53 located in a substantially horizontal position as shown in FIGS. 1 and 5. The size and rate of the spring is a function of the weight of the radiographic head 13 whose weight must be counterbalanced as the head 13 is moved from its normal position where mounting members 18 are positioned vertically as shown in FIG. 1.

Figure 3:
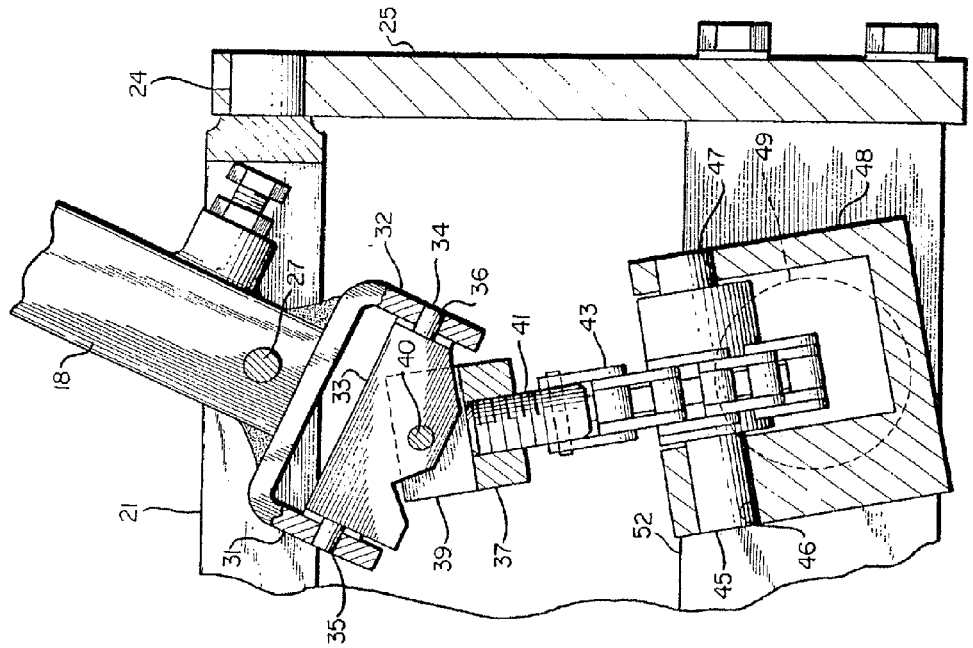
FIG. 3 is a fragmentary section view of the mounting assembly of FIG. 2 but with vertical mounting members pivoted at an acute angle from the vertical axis whereby the radiographic device is disposed closer to the patient foot platform than the normal position of FIG. 2.
Figure 4:
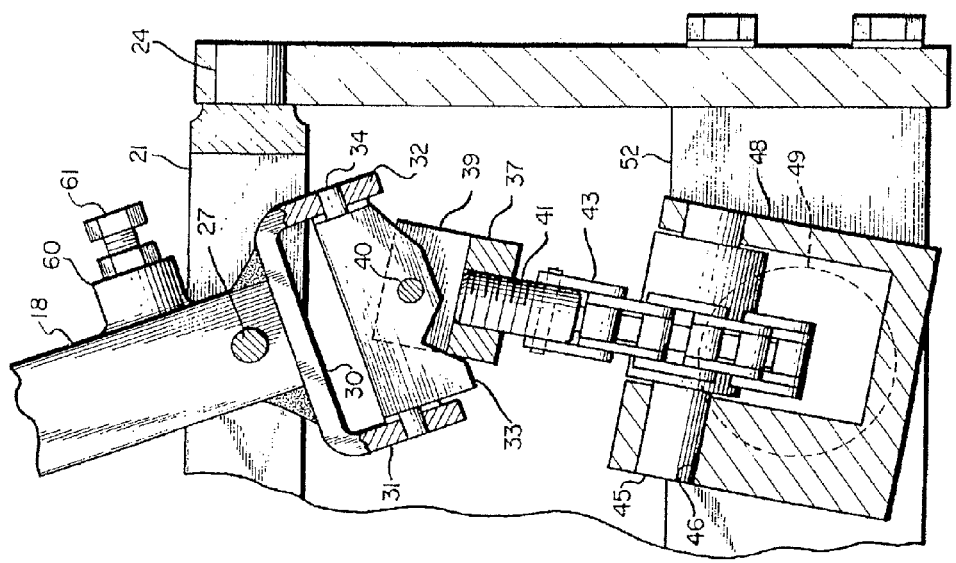
FIG. 4 is a fragmentary section view of the mounting assembly of FIG. 2 in which the vertical mounting members are disposed at acute angles opposite those shown in FIG. 3.

Referring to FIGS. 3 and 4, an adjustable first stop means 60 having an adjustable bolt 61 is attached to one of the mounting members 18 contiguous to end 20 (FIG. 2) and serves to limit the amount that the mounting members 18 can pivot about pins 27, 28. As seen in FIG. 4, the adjustment of pin 61 serves to control the amount that the mounting members 18 will pivot about pins 27, 28 in the direction of arrow "R" (FIG. 1) until bolt 61 abuts the trunion 21. The mounting members 18 can pivot in the direction of the arrow "Q" shown in FIGS. 1 and 2 until one of the mounting members 18 abuts the mounting plate 26 which, as shown in FIG. 2, is taller than the mounting plate 25. Accordingly, the amount of displacement of the radiographic head 13 afforded by the mounting assembly as shown in FIGS. 2-4 in the directions of the arrows of "Q" and "R" is limited.

The extent that the mounting members 18 can pivot in the directions of arrows "S" and "T", as shown in FIG. 1, is controlled by a stop means 64 (FIG. 5), which comprises a stop arm 65 which extends outward from the pivotable trunnion 21 at a location on the frame contiguous to the mounting plate 26. A stop lug 67 projects outward from the plate 26 and serves to act as a stop, FIG. 6, such that when the arm 65 contacts the stop lug 67, the mounting members 18 are precluded from further pivotal movement in the direction of the arrow "S" shown in FIGS. 1 and 5.

A second stop lug 68 shown in FIG. 5 projects outward from the plate 26 and serves to abut the arm 65, whereby the amount that the mounting members 18 can pivot in the direction of arrow "T", as shown in FIGS. 1 and 5, also is limited.

Viewing FIGS. 2-4 and 5-7, it will be appreciated that the vertical mounting members 18 will rotate about the axes "Q" and "R" (FIGS. 2-4) and "S" and "T" (FIGS. 5-7) as illustrated by phantom lines in FIG. 8. There are occasions, however, when the radiographic head 13 must be rotated to a different position which requires the head 13 to be pivoted to a position such as illustrated by the phantom lines in FIG. 8. The mounting assembly will permit such movement; however, it has been found that the chain 43 has a tendency to twist when moved to a position off of the Q-R and S-T axes, the effect of which is to place an undesired torsional force upon the chain 43. This force is avoided, however, because the fastener 41, which is threaded into the yoke 37, is adapted to rotate as illustrated, for example, by the arrow "X" whereby the chain 43 will not be twisted substantially such that an undesired torsional force is avoided.

The pivotable yokes 30 and 37 and blocks 33 and 48 facilitate the desired articulation of the radiographic head 13 without extensive movement of the chain 43. Referring to FIGS. 2 and 3, it will be noted that the pin 40 moves a relatively small amount relative to the movement of the radiographic head 13 such that extensive displacement of the chain 43 does not occur.

FIGS. 5, 6, and 7 show displacement of the mounting members 18 relative to their vertical axes in the direction of the arrows "S" and "T". The double yokes 30 and 37 and pivotable blocks 33 and 48 permit a relatively small amount of movement of the pin 34 in comparison to the displacement of the radiographic head 13 such that only a relatively small displacement of the chain 43 occurs.

The radiographic device 8 as described to this point is conventional, and includes a linkage system having a pivot point that is offset with respect to a lateral reference line 80 that intersects a center of rotation "CR" of the sprocket 44. As best shown in FIGS. 5-7, the chain 43 includes several links 81 joined by pins 82. The chain includes a transitional link 81a, which joins a chain distal portion 43a that is entrained about the sprocket 44 and is coupled to the spring, and a chain proximal portion 43b that is not entrained about the sprocket 44 and is coupled to the yoke 37. The transitional link 81a includes pivot pin 82a which defines the point at which the chain proximal portion 43b is free to pivot with respect to the chain distal portion 43a, thereby to accommodate movement of the mounting members 18.

Movement of the mounting members 18 from the normal, vertical position creates tension in the chain 43 and consequently increases the balance force exerted by the spring of the spring assembly 53. With the pivot pin 82a offset from the lateral reference line 80 by a distance "D", the chain 43 will move less when the mounting members 18 are moved in the "T" direction than when they are moved in the "S" direction. As a result, the spring assembly 53 exerts a greater force when the mounting members 18 move in the "T" direction and a lesser force when the mounting members 18 are moved in the "S" direction.

This force differential may result in unintended movement of the radiographic head 13 after it is positioned and released by the technician. For example, if the spring is adjusted so that it accurately holds the mounting members 18 when moved in the "S" direction, it will tend to exert too much force when the mounting members 18 are moved in the "T" direction, thereby causing the mounting members 18 to move at least partially back toward the normal position when the radiographic head is released. Conversely, if the spring is selected so that it accurately holds the mounting members 18 when moved in the "T" direction, it will tend to exert too little force when the mounting members 18 are moved in the "S" direction, thereby causing the mounting members 18 to fall further in the "S" direction under the weight of the radiographic head 13. Such unintended drifting of the radiographic head 13 may result in image inaccuracies due to poor head angles or require additional time and care to reposition the head in the desired location.

Figure 9:
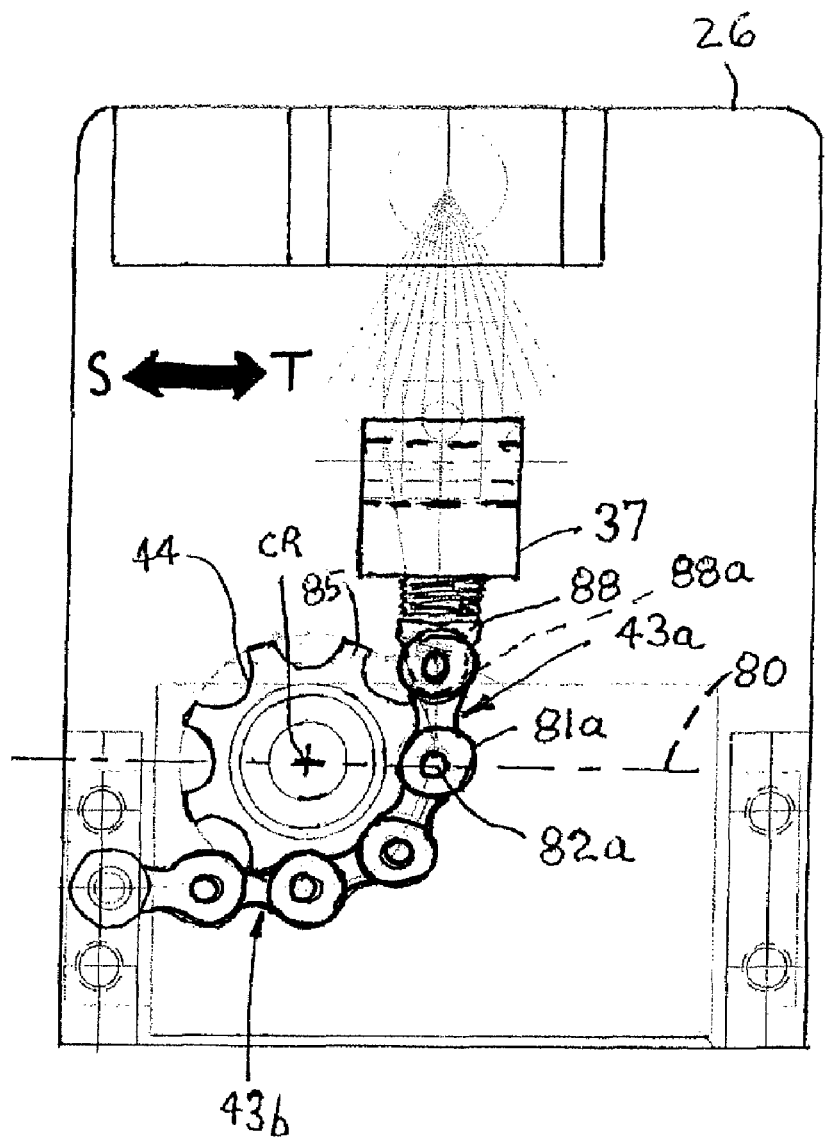
FIG. 9 is a fragmentary section view of the mounting assembly of the current disclosure with the support arm assembly in the normal position.

The present disclosure addresses the force differential problem described above by aligning a pivot point of the chain 43 with the lateral reference line 80 when the mounting members 18 are in the normal position. As shown in FIG. 9, the chain 43 and sprocket 44 are rotated from the conventional position shown in FIG. 5 so that the pivot pin 82a lies along the lateral reference line 80, and therefore is horizontally aligned with the sprocket center of rotation "CR." As a result, the chain 43 will move substantially the same distance when the mounting members 18 are rotated in both the "S" and "T" directions, thereby minimizing the force differential that the spring must accommodate and allowing for use of longer mounting members 18, which may increase the SID to approximately 40 inches or more.

Additionally modifications may be made to the linkage system to accommodate the change in orientation of the sprocket 44 and the chain 43. Because the pivot pin 82a is moved further down, there is an increased possibility that one or more teeth of the sprocket 44 will interfere with the chain proximal end 43a when the mounting members rotate in the "S" direction. Accordingly, some of the teeth 85 of the sprocket may be modified to have a reduced profile, thereby to provide additional clearance for movement of the chain proximal end 43a.

Additionally, the linkage system may include a modified clevis pin 88 for attaching the chain proximal end 43a to the second yoke 37. More specifically, the clevis pin 88 may have a rounded head 88a sized to fit within a gap between adjacent teeth 85 of the sprocket 44, thereby to allow the clevis pin 88 to become at least partially entrained in the sprocket 44 when the mounting members 18 move to an extreme lateral position (in either the "S" or "T" directions).

While only certain embodiments have been set forth, alternatives and modifications will be apparent from the above description to those skilled in the art. These and other alternatives are considered equivalents and within the spirit and scope of this disclosure and the appended claims.

What is claimed:

1. A radiographic device comprising:
   a base;
   a support arm pivotably coupled to the base and defining a support axis, the support arm being movable between a normal position and two diametrically opposed, laterally rotated positions;
   a radiographic head coupled to the support arm;
   a tension assembly coupled to the base; and
   a linkage system extending between the tension assembly and the support arm, the linkage system including:
      a hub rotatably coupled to the base and defining a center of rotation with which a lateral reference line intersects;
      a linkage partially entrained with the hub and having a proximal end adapted for coupling to the support arm and a distal end adapted for coupling to the tension assembly, the linkage including a pivot point joining the linkage proximal end and the linkage distal end;
      wherein, when the support arm is in the normal position, the linkage is positioned with respect to the hub so that the lateral reference line also intersects the linkage pivot point.

2. The radiographic device of claim 1, in which the support arm comprises a pair of support members.

3. The radiographic device of claim 1, in which the support arm is in the normal position when the support arm axis is substantially vertical.

4. The radiographic device of claim 1, in which the pivot point comprises a pin that pivotably couples the linkage proximal end to the linkage distal end.

5. The radiographic device of claim 4, in which the linkage comprises a chain.

6. The radiographic device of claim 1, in which the lateral reference line is substantially horizontal.

7. The radiographic device of claim 1, in which the support arm has a length of at least approximately 40 inches.

8. The radiographic device of claim 1, in which the hub comprises a sprocket.

9. The radiographic device of claim 1, in which the tension assembly comprises a spring.

10. A linkage system for a radiographic device having a base, a support arm pivotably coupled to the base and defining a support axis, the support arm being movable between a normal position and two diametrically opposed, laterally rotated positions, a radiographic head coupled to the support arm, and a tension assembly coupled to the base, the linkage system extending between the tension assembly and the support arm and comprising:

a hub rotatably coupled to the base and defining a center of rotation with which a lateral reference line intersects;

a linkage partially entrained with the hub and having a proximal end adapted for coupling to the support arm and a distal end adapted for coupling to the tension assembly, the linkage including a pivot point joining the linkage proximal end and the linkage distal end;

wherein, when the support arm is in the normal position, the linkage is positioned with respect to the hub so that the lateral reference line also intersects the linkage pivot point.

11. The linkage system of claim 10, in which the support arm comprises a pair of support members.

12. The linkage system of claim 10, in which the support arm is in the normal position when the support arm axis is substantially vertical.

13. The linkage system of claim 10, in which the pivot point comprises a pin that pivotably couples the linkage proximal end to the linkage distal end.

14. The linkage system of claim 13, in which the linkage comprises a chain.

15. The linkage system of claim 10, in which the lateral reference line is substantially horizontal.

16. The linkage system of claim 10, in which the support arm has a length of at least approximately 40 inches.

17. The linkage system of claim 10, in which the hub comprises a sprocket.

18. The linkage system of claim 10, in which the tension assembly comprises a spring.

\* \* \* \* \*